United States Patent
Teo

Patent Number: 6,120,455
Date of Patent: Sep. 19, 2000

[54] METHODS AND APPARATUS FOR NON-UNIFORM ROTATION DISTORTION DETECTION IN AN INTRAVASCULAR ULTRASOUND IMAGING SYSTEM

[75] Inventor: Tat-Jin Teo, Sunnyvale, Calif.

[73] Assignee: SciMed Life Systems, Inc., Maple Grove, Minn.

[21] Appl. No.: 09/250,462

[22] Filed: Feb. 16, 1999

Related U.S. Application Data

[63] Continuation of application No. 08/977,543, Nov. 25, 1997.

[51] Int. Cl.[7] .................................................. A61B 08/00

[52] U.S. Cl. ........................................... 600/468; 600/467

[58] Field of Search ................................... 600/443, 468, 600/459, 466, 461, 462, 467

[56] References Cited

U.S. PATENT DOCUMENTS

| | | | |
|---|---|---|---|
| 5,377,682 | 1/1995 | Ueno et al. | 128/660.1 |
| 5,385,725 | 1/1995 | Lin et al. | 424/9 |
| 5,438,997 | 8/1995 | Sieben et al. | 600/463 |
| 5,442,155 | 8/1995 | Sieben | 600/443 |
| 5,443,457 | 8/1995 | Ginn et al. | 600/463 |
| 5,476,096 | 12/1995 | Olstad et al. | 128/660.07 |
| 5,485,845 | 1/1996 | Verdonk et al. | 128/662.06 |
| 5,713,363 | 2/1998 | Seward et al. | 128/662.06 |

OTHER PUBLICATIONS

Petros Maragos, "Morphological Correlation and Mean Absolute Error Criteria," *IEEE*, 1989, pp. 1568–1571.

Daniel I. Barnea and Harvey F. Silverman, "A Class of Algorithms for Fast Digital Image Registration," *IEEE Transactions on Computers*, vol. C–21, No. 2, Feb. 1972, pp. 179–186.

*Primary Examiner*—Marvin M. Lateef
*Assistant Examiner*—Maulin Patel
*Attorney, Agent, or Firm*—Townsend and Townsend and Crew LLP

[57] ABSTRACT

Methods and apparatus for non-uniform rotation distortion detection for enhanced intravascular ultrasound imaging. The present invention provides methods and apparatus which detect non-uniform rotation in an improved manner without using beacons which may create shadowing of tissue behind the beacons or other undesired artifacts in the image. In specific embodiments, the present invention may provide a particularly simple and useful solution for addressing the problem of non-uniform rotation distortion in intravascular ultrasound imaging in systems which use mechanical scanning. In specific embodiments, the present invention utilizes correlation of received signals in an image vector from reverberating ultrasound in a bubbly liquid-flushed catheter to determine non-uniform rotation of the transducer within the catheter. In other embodiments, the present invention utilizes correlation of imaging vectors within a blood speckle region given a particular beamwidth of ultrasound energy from a transducer to determine non-uniform rotation of the transducer.

21 Claims, 8 Drawing Sheets

The present invention provides methods and apparatus for non-uniform rotation distortion detection in an intravascular ultrasound imaging system.

METHODS AND APPARATUS FOR NON-UNIFORM ROTATION DISTORTION DETECTION IN AN INTRAVASCULAR ULTRASOUND IMAGING SYSTEM

This application is a continuation of and claims the benefit of U.S. Application Ser. No. 08/977,543, filed Nov. 25, 1997, the disclosure of which is incorporated by reference.

BACKGROUND OF THE INVENTION

The present invention relates to high resolution intravascular imaging and more particularly to intravascular ultrasound imaging and techniques for enhancing image quality.

In intraluminal or intravascular ultrasound (also referred to as "IVUS") imaging, the production of high resolution images of vessel wall structures requires imaging at high ultrasound frequencies. IVUS imaging systems may utilize electronic scanners or mechanical scanners. IVUS systems utilizing electronic scanning typically include in the distal end of a catheter an array of ultrasound transducers which are sequentially excited so as to electronically scan an ultrasonic beam. IVUS systems utilizing mechanical scanning (one example of such a system being shown in FIG. 1) may use a single rotating transducer 1 in the distal end of a catheter 3 that enters the blood vessel 20, with a drive shaft 5 coupling the transducer 1 to a motor (not shown) coupled to the catheter 3 at its proximal end. IVUS systems using mechanical scanning have wider applications, mainly due to the smaller size of the mechanical scanner in comparison with electronic scanner, that advantageously allow the system to be used for smaller blood vessels as well as larger blood vessels.

The present invention relates to IVUS imaging systems with mechanical scanning. In these types of IVUS systems, an ultrasonic unidirectional exciter/detector (e.g., transducer) within a catheter probe positioned within a blood vessel is used to acquire signal data from echoes of the emitted ultrasonic energy off the interior of the blood vessel. Specifically, vectors are created by directing focused ultrasonic pressure waves 2 radially from a transducer in a catheter and collecting echoes 4 at the same transducer from the target area, as seen in FIG. 1. In an exemplary IVUS system with mechanical scanning, the transducer is mechanically rotated at a uniform speed with multiple firings of ultrasonic excitation in order to obtain a plurality of equally spaced radial vectors from the collected echoes. The plurality of radial vectors from the rotated transducer comprises an image frame. A signal processor then performs image processing (e.g., stabilization of a moving image, temporal filtering for blood speckle, and other image enhancement techniques) on the acquired data in order to provide a display of the corrected and filtered intravascular image on a raster-scan display monitor. Signal processing in an intravascular ultrasound imaging system utilizing a mechanically rotated transducer operates under the assumption that the transducer is rotated at a uniform speed. However, this assumption is often violated as the catheter traverses the blood vessel. Specifically, the friction between the catheter and the vessel walls and/or the flexing of the vessel walls causes binding and/or whipping of the catheter, which translates into non-uniform rotation of the transducer. The system thus inaccurately reads the reflected echoes from blood/vessel structure/blood vessel as being received from an incorrect location, as the assumption of uniform rotational speed is violated. Therefore, it is desirable to detect and quantize the non-uniform rotation in order to correct for the image distortion caused by non-uniform rotation, and thereby provide an intravascular image display with enhanced accuracy.

Some conventional techniques used to detect non-uniform rotation of the transducer in intravascular ultrasound imaging involve calibrating the catheter 3 with landmarks or beacons 7, whether active or passive, generally located at various points (circumferentially or helically) along the perimeter of sheath 9 of the catheter 3, as seen in FIG. 1. Each beacon's position relative to the catheter is known. Passive beacons act as reflectors of ultrasound transmitted by the catheter and may undesirably cause reflective bright spots on the image which shadow points in the intravascular field behind the spots. Active beacons transmit ultrasonic energy (characterized by phase, amplitude, frequency and/or pulse repetition rate so as to identify the particular beacon) in the direction of the rotating transducer so that the imaging system may identify the particular beacon in order to determine the angular position of the transducer. However, such conventional techniques using passive or active beacons are not always effective because the beacons may cause shadowing of tissue behind the beacons or may introduce artifacts adversely affecting the imaging of the anatomical structures.

From the above, it can be seen that alternative methods and apparatus are needed for detecting non-uniform rotation distortion to allow enhanced display of intravascular ultrasound images.

SUMMARY OF THE INVENTION

The present invention provides methods and apparatus which detect non-uniform rotation in an improved manner without using beacons which may create shadowing of tissue behind the beacons or other undesired artifacts in the image. In specific embodiments, the present invention may provide a particularly simple and useful solution for addressing the problem of non-uniform rotation distortion in intravascular ultrasound imaging in systems which use mechanical scanning.

According to a specific embodiment, the present invention provides a method for detecting non-uniform rotation distortion in an intravascular ultrasound blood vessel image. The method includes the step of providing a catheter probe within a blood vessel, where the catheter probe includes a sheath and a transducer substantially centrally located within the sheath. The transducer is mechanically controlled and the catheter probe also includes a bubbly liquid between the sheath and the transducer. The method also includes the steps of emitting an ultrasonic beam to produce echoes reflected from the bubbly liquid and the sheath to obtain a given image vector, and sampling the echoes in multiple time windows for the given image vector. In addition, the method includes the step of correlating the sampled echoes in the multiple time windows to determine existence of non-uniform rotational speed of the transducer.

According to another specific embodiment, the present invention provides a method for detecting non-uniform rotation distortion in an intravascular ultrasound blood vessel image. The method provides a catheter probe within a blood vessel, where the catheter probe has a transducer substantially centrally located therein and the transducer is mechanically controlled. The method also provides steps of emitting multiple ultrasonic beams to produce echoes reflected from a blood region within the blood vessel to obtain multiple successive image vectors, and sampling the echoes at a predetermined range ($r_P$) for each of the successive image vectors. The $r_P$ for each of the successive image vectors is located within the blood region. The method further includes obtaining correlation coefficients for the sampled echoes at $r_P$ between each of the successive image vectors to determine changes in a rotational speed of the transducer.

According to another specific embodiment, the present invention provides related apparatus and other methods for detecting non-uniform rotation distortion in an intravascular ultrasound blood vessel image utilizing correlation. These and other embodiments of the present invention, as well as its advantages and features, are described in more detail in conjunction with the text below and attached figures.

DESCRIPTION OF THE SPECIFIC EMBODIMENTS

The present invention provides for detection of non-uniform rotation distortion for enhanced image processing in intravascular ultrasound imaging systems. The present invention provides image processing methods which may be used to detect non-uniform rotation distortion in the displayed image with the intravascular ultrasonic imaging system (shown in FIG. 2) which uses mechanical scanning without active or passive beacons.

Figure 1:
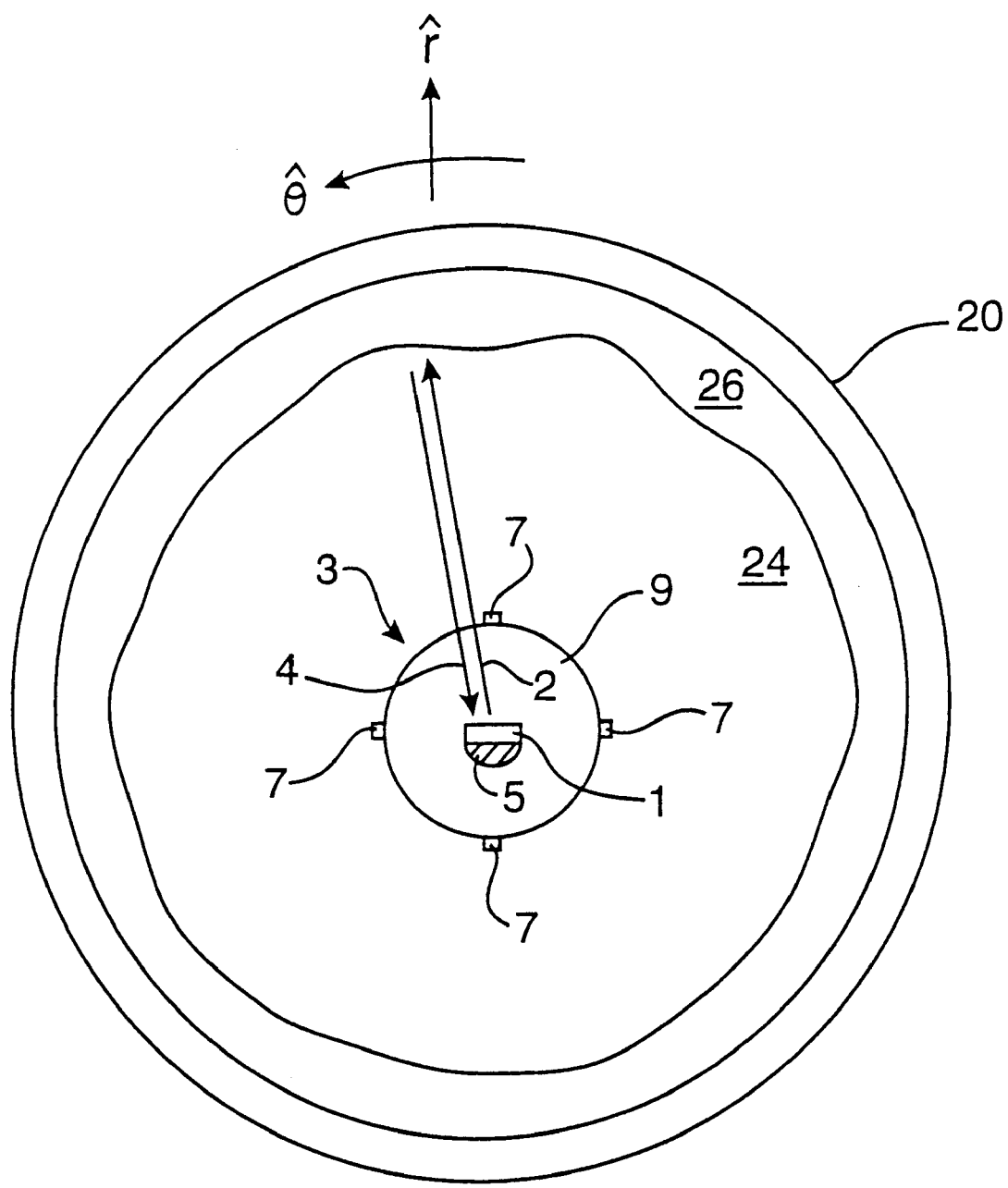
FIG. 1 is a cross-sectional view of a blood vessel and a catheter probe therein of an exemplary IVUS system utilizing mechanical scanning, in accordance with the prior art.
Figure 2:
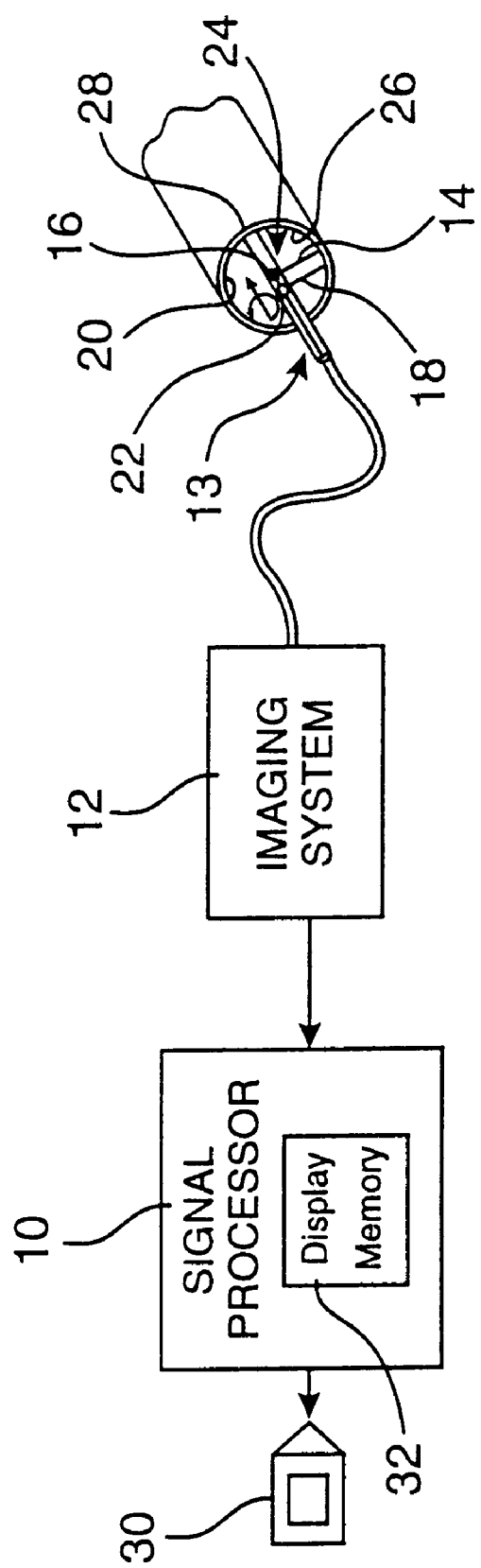
FIG. 2 is a block diagram of an intravascular ultrasonic imaging system in accordance with a specific embodiment of the present invention.
Figure 3:
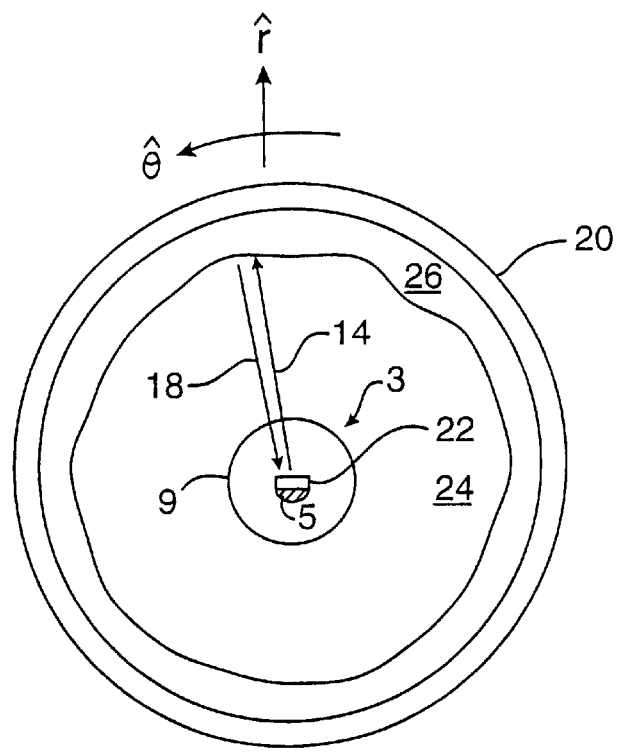
FIG. 3 is a cross-sectional view of a blood vessel and a catheter probe therein of an IVUS system utilizing mechanical scanning, in accordance with the present invention.

Referring to FIG. 2, there is shown a block diagram of a type of intravascular ultrasonic imaging system 10 that may be used for intravascular image display in accordance with a specific embodiment of the present invention. FIG. 3 illustrates a cross-sectional view of a blood vessel and a catheter probe therein of an IVUS system utilizing mechanical scanning in accordance with the present invention. As seen in FIG. 2, a specialized signal processing device 10 is used with an ultrasonic imaging system 12 including a catheter probe 13 wherein ultrasonic beams 14 are emitted by an ultrasonic transmitter or exciter 16 of transducer 22, which is at the distal end of catheter 13 and is coupled via drive shaft 5 to a motor (not shown) at the proximal end of catheter 13. The ultrasonic signals 14 of, for example, 5 Megahertz (MHz) to 50 MHz, are directed to an intravascular target to cause reflections in the form of ultrasonic echo signals 18 from the intravascular structures, including blood. Radial spokes or vectors 18 of information are collected from a target 20 (the interior walls of a blood vessel) based on ultrasonic reflections received at a transducer 22. Specifically, information is gathered by projecting narrow ultrasonic sampling beams 14 (of a predetermined beamwidth) from exciter 16 as it is rotated (by an angle θ) within catheter 13 in blood vessel 20. The reflections scale in amplitude over a range and are recorded by transducer 22 as a function of unit distance (r) along the radius of each vector. The image is representative of a cross-sectional "slice" of the structure of blood vessel 20 and includes wall structures (blood-wall interface) 26 and lumens of blood (blood region) 24, as seen in FIGS. 2 and 3. This image data may be acquired as either analog or digital information, depending on the specific system utilized. The data acquired is converted into pixels representing points in a scanned (swept or rotated) two-dimensional image. These pixels are assigned a value on, for example, a gray scale between black and white. Of course, the assigned value may be on a color scale in other embodiments. After the intravascular ultrasonic imaging system acquires the image data, signal processor 10 performs signal processing of the acquired image data and scan-converting the image data into x-y rasterized image data for storing into display memory 32 and then providing the raster image for viewing on a display device 30 coupled to signal processor 10. Signal processor 10 also includes a program memory 38 which may be used to store the computer-readable program(s) for implementing specific embodiment(s) of the present invention, as discussed further below. Alternatively, the computer-readable program(s) for implementing specific embodiments of the present invention may be stored on a memory coupled to signal processor 10. For example, the memory may be a read-only memory, fixed disk drive, or removable disk drive.

In the IVUS system shown in FIGS. 2 and 3, transducer 22 is mechanically rotated within sheath 9 of catheter 13 at a uniform speed of, for example, about 1800 revolutions per minute with about 300 firings of ultrasonic excitation in order to obtain a plurality of equally spaced radial vectors from the collected echoes for an image frame. For each ultrasonic beam fired, the amplitude for a particular distance r in the radial vector is obtained by sampling the reflections received at transducer 22, where $r=(tc)/2$ (where t is the time between the firing of the ultrasonic beam and the receipt of the particular amplitude being sampled, and c is the speed of sound in the blood/tissue/water medium, which may be about 1500 meters/second±20% variation depending, among other factors, on the temperature and type of the medium). Intravascular image frames are obtained by sampling reflections received at transducer 22 for $r>r_s$, where $r_s$ is the distance between transducer 22 and sheath 9 of catheter 13.

Figure 4:
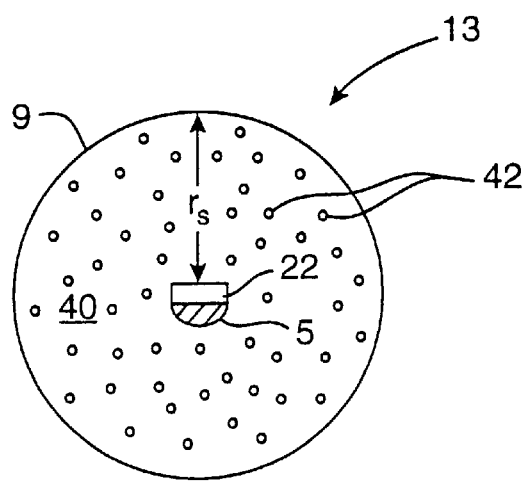
FIG. 4 is a cross-sectional detailed view of a catheter probe with a bubbly liquid contained therein, according to a specific embodiment of the present invention.

According to a specific embodiment of the present invention, catheter 13 is flushed with bubbly liquid containing, for example, micro-bubbles, as seen in FIG. 4. FIG. 4 is a cross-sectional detailed view of a catheter probe with a bubbly liquid contained therein, according to this specific embodiment of the present invention. In the present embodiment, sheath 9 is as non-reflective (i.e., as transmissive) of ultrasounds as possible so that ultrasounds may be emitted through sheath 9 and echoes may be received through sheath 9 for imaging purposes. However, for purposes of non-uniform rotation detection, at least some portion of sheath 9 is reflective of ultrasound to provide the ultrasound reverberation utilized in the present embodiment. For example, a first portion along the length of sheath 9 that is ultrasound transmissive may be used for imaging purposes while a second portion along the length of sheath 9 that is ultrasound reflective may be used for non-uniform rotation purposes. By flushing catheter 13 with liquid 40 which contains micro-bubbles 42, a reverberation of ultrasound is created between transducer 22 and sheath 9. Albunex™ available from Molecular Bioscience Inc. or Taligent™ available from Alliance Pharmaceutical are exemplary bubbly liquids which may be used in the present invention as a contrast agent. Micro-bubbles 42 useful with the present embodiment have a mean diameter on the order of about 4 $\mu$m or less with a distribution ranging between about 1–10 $\mu$m. Transducer 22 thus receives multiple echoes from sheath 9 and micro-bubbles 42 arising from different round trips of the ultrasonic beam echoed within sheath 9.

Figure 5A:
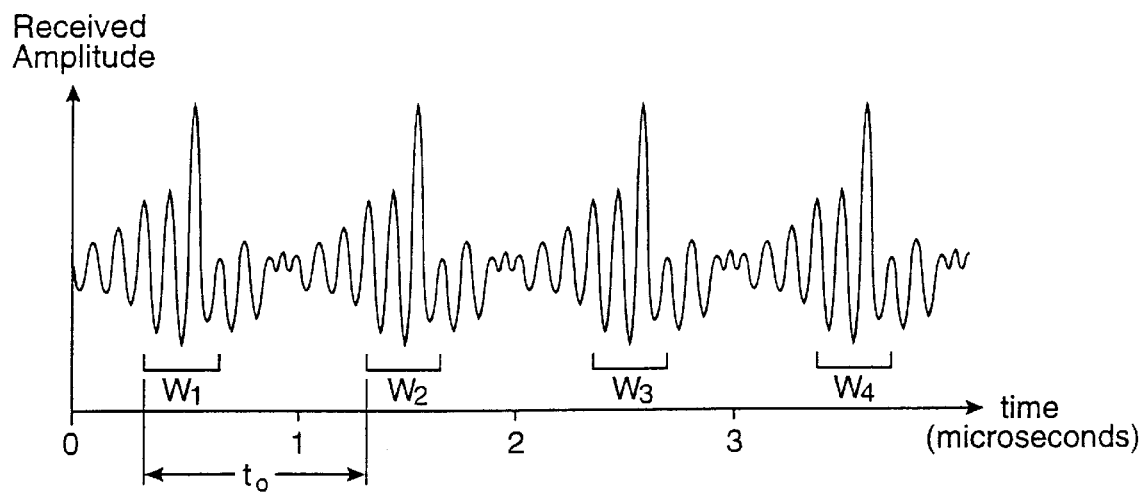
FIGS. 5(a) and 5(b) are exemplary diagrams of the amplitude of multiple echoes received at transducer 22 in relation with time corresponding to distance $r<r_s$ when transducer 22 has uniform rotation and non-uniform rotation, respectively, in accordance with the specific embodiment of FIG. 4.
Figure 5B:
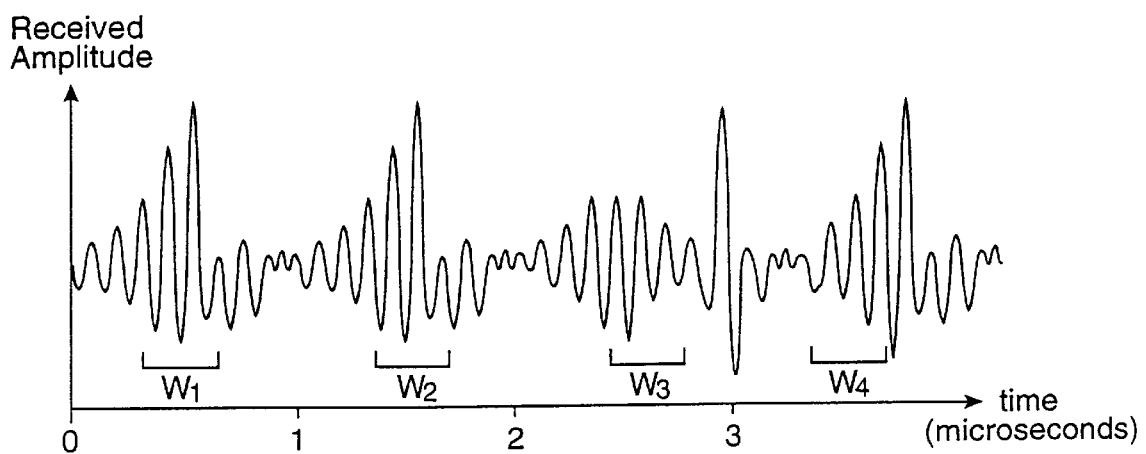

In accordance with the present embodiment of FIG. 4, FIGS. 5(a) and 5(b) are exemplary diagrams of the amplitude of these multiple echoes received at transducer 22 in relation to time corresponding to distance $r<r_s$ when transducer 22 has uniform rotation and non-uniform rotation, respectively. According to the present embodiment, equally spaced segments (amplitude in the time/depth dimension) along an imaging vector within $r_s$ would be correlated with one another. Since the deeper segments of the imaging vector came from multiple round trips of ultrasound between transducer 22 and sheath 9, the correlation or the lack thereof in the different segments of the received signal is a measure of the rotational speed. For a non-rotating environment, the correlation between two segments of the imaging vector arising from different round trips between transducer and the sheath would be high. For example, as seen in FIG. 5(a), equally spaced segments in the image vector are shown as windows ($w_1$, $w_2$, $W_3$, and $w_4$) in time. The time $t_o$ between the beginning of a window and the beginning of the next successive window is preferably greater than the time $t_s=(2\ r_s)/c$ between an ultrasonic beam being emitted by the transducer and a first echo received by the transducer. Each time window should be as short as possible but have a sufficient width (i.e.g, time duration) to capture enough information from an echo in order to perform an adequate correlation. In the example of FIG. 5(a), correlating each of the segments of the image vector with the preceding segment results in correlation coefficients of about 0.72, 0.71 and 0.73 for $w_2$, $w_3$, and $w_4$, respectively. Thus, the highly correlated segments indicate that transducer 22 is rotating in a substantially uniform manner. Any rotational non-uniformity of transducer 22 would manifest itself as a notable change in the correlation coefficient in segments of the imaging vector. In particular, an increase in the correlation coefficient from window to successive window would indicate that the transducer's rotational motion has slowed down, and a decrease in the correlation coefficient from window to successive window would indicate that the transducer's rotational motion has sped up. In the example of FIG. 5(b), correlating each of these segments of the image vector with the successive segment results in correlation coefficients of about 0.73, 0.53 and 0.91 for $w_2$, $w_3$, and $w_4$, respectively. As seen in FIG. 5(a)–5(b), non-uniform rotation, more specifically, an increase in the transducer's rotational speed, has occurred from window $w_3$ to $w_2$; while non-uniform rotation, more specifically, a decrease in the transducer's rotational speed, has occurred from window $w_4$ to $w_3$. The present embodiment is suitable for use with catheters where the distance $r_s$ between sheath 9 and transducer 22 is large enough to provide for close ultrasound reverberations with each window being sufficiently wide so as to capture only one reverberation. For example, a catheter having a transducer small in size compared to the sheath, which would have dimensions as required for the particular intravascular application, may be useful for the present embodiment.

In accordance with other specific embodiments using a liquid-flushed catheter 13 with the liquid being filled with micro-bubbles, correlation over larger time separation can also be performed across different segments in different imaging vectors. If transducer 22 is rotating with uniform speed, the correlation coefficient will remain the same for a given separation in time and beamwidth. Multiple correlation coefficients for a given time separation can be made and the average can be used to improve the accuracy of the measurement, in other embodiments.

Examples of correlation techniques which may be used in accordance with the present invention are discussed in detail by Daniel I. Barnea and Harvey F. Silverman in an article entitled "A Class of Algorithms for Fast Digital Image Registration," on pages 179–186 of the *IEEE Transactions on Computers*, Vol. C-21, No. 2, February 1972, and by Petros Maragos in an article entitled "Morphological Correlation and Mean Absolute Error Criteria," on pages 1568–1571 of the *IEEE Proceedings*1989 *of the International Conference on Acoustic Speech and Signal Processing*. Both articles are herein incorporated by reference for all purposes. For example, the specific embodiments discussed above (for example, the embodiments relating to FIG. 4) could utilize the general correlation expression given in equation 6 or 11 of the Barnea reference, but in the 1-dimensional time/depth domain.

Figure 6A:
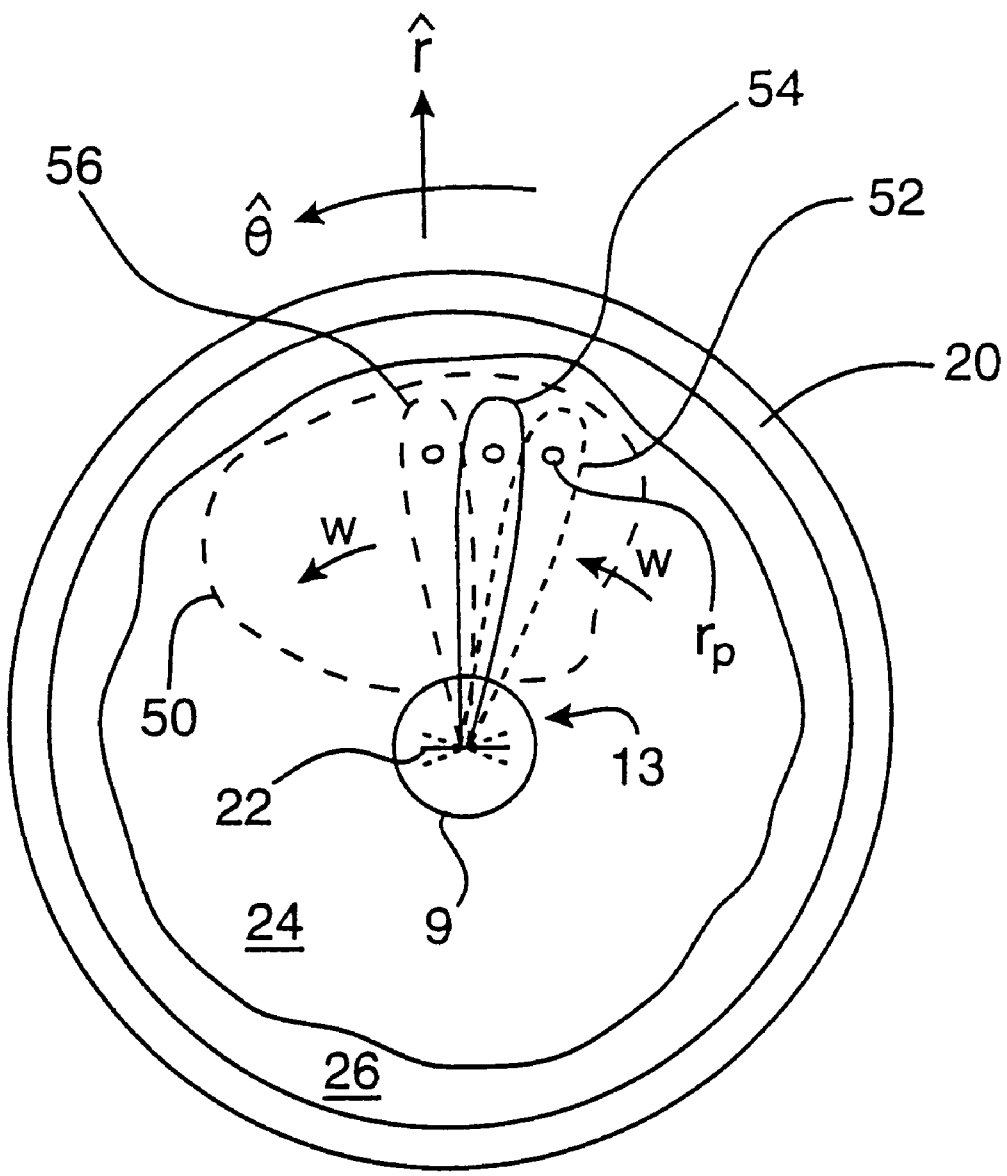
FIG. 6(a) is an exemplary diagram illustrating successive vectors for a transducer rotating uniformly, according to another specific embodiment of the present invention.

According to another specific embodiment, the present invention uses correlation of blood speckle to track the rotation of the transducer. This embodiment could utilize the general correlation expression given in equation 6 or 11 of the Barnea reference, in the 1-dimensional time/depth domain for a given depth ($r_P$) in successive image vectors. According to this embodiment, a region 50 in the imaging scene where the image texture is full of speckle is selected. Within blood speckle region 50, the correlation coefficient should be low for respective points $r_P$ (in successive image vectors) that are separated from each other by greater than the ultrasound beamwidth (measured in angle); whereas, within blood speckle region 50, the correlation coefficient should be high for respective points $r_P$ (in successive image vectors) that are separated from each other by less than the ultrasound beamwidth. FIG. 6(a) is an exemplary diagram illustrating successive vectors for a transducer 22 rotating uniformly, according to this specific embodiment. For simplicity, the transducer 22 is located substantially in the center of blood vessel 20, but it should be recognized that the discussion also applies when transducer 22 is off-center as long as region 50 of blood speckle exists for use with the present embodiment. As seen in FIG. 6(a), transducer 22 is rotating with a uniform rotational speed $\omega$ with successive image vectors (specifically, image vector 52 taken for $\theta_i$, image vector 54 taken for $\theta_{i+1}$, and image vector 56 taken for $\theta_{i+2}$) being uniformly separated by a uniform angular separation $\Delta\theta$. The correlation between each successive image vector (between 52 and 54, and between 54 and 56) at the same predetermined range $r_P$ (we define this correlation for uniformly rotating speed $\omega$ to be $C_\omega$) should be relatively high and substantially similar between successive image vectors which maintain about the same angular separation. The lack of fluctuation of the correlation coefficient in successive imaging vectors indicates a lack of fluctuation (i.e., uniform rotation) in the rotational speed of transducer 21.

Figure 6B:
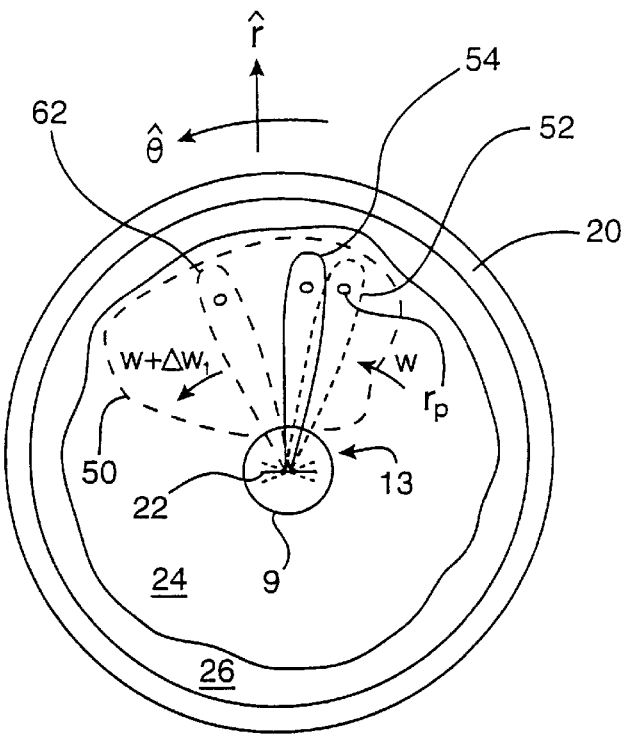
FIGS. 6(b)–6(c) are exemplary diagrams illustrating successive vectors for a non-uniformly rotating transducer which is increasing and decreasing, respectively, in rotational speed in comparison to the uniform rotational speed shown in FIG. 6(a).
Figure 6C:
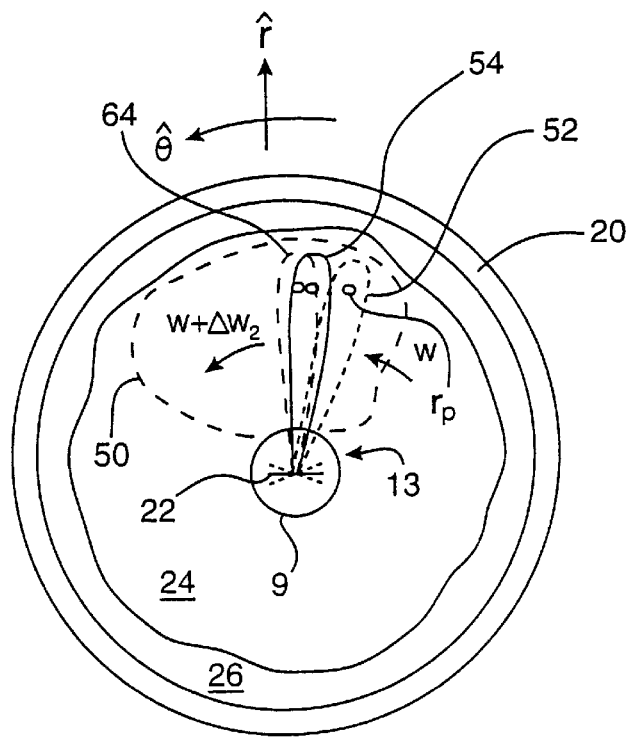

FIGS. 6(b)–6(c) are exemplary diagrams illustrating successive vectors for a non-uniformly rotating transducer which is increasing and decreasing, respectively, in rotational speed in comparison to the uniform rotational speed shown in FIG. 6(a). As seen in FIG. 6(b), transducer 22 rotates with a uniform rotational speed $\omega$ from image vector 52 taken for $\theta_i$ to image vector 54 taken for $\theta_{i+1}$, which are uniformly separated by a uniform angular separation $\Delta\theta$. However, transducer 22 starts to rotate with an increasing rotational speed $\omega+\Delta\omega_1$ from image vector 54 taken for $\theta_{i+1}$ to image vector 62 taken for $\eta_{i+2}$. The correlation between successive image vectors 52 and 54 at the same predetermined range rp should be relatively high and is defined by $C_\omega$. However, the correlation between successive image vectors 54 and 62 at the same predetermined range $r_P$ should be lower than the correlation $C_\omega$ between vectors 52 and 54, since successive image vectors 54 and 62 have a wider angular separation compared to the beamwidth. The decrease of the correlation coefficient from $C_\omega$ in successive imaging vectors indicates an increase in the rotational speed of transducer 21.

In FIG. 6(c), transducer 22 rotates with a uniform rotational speed $\omega$ from image vector 52 taken for $\theta_i$ to image vector 54 taken for $\theta_{i+1}$, which are uniformly separated by a uniform angular separation $\Delta\theta$. However, transducer 22 starts to rotate with a decreasing rotational speed $\omega-\Delta\omega_2$ from image vector 54 taken for $\theta_{i+1}$ to image vector 64 taken for $\theta_{i+2}$. Again, the correlation between successive image vectors 52 and 54 at the same predetermined range $r_P$ should be relatively high and is defined by $C_\omega$. However, the correlation between successive image vectors 54 and 64 at the same predetermined range $r_P$ should be higher than the correlation $C_\omega$ between vectors 52 and 54, since successive image vectors 54 and 64 have an even smaller angular separation compared to the beamwidth than image vectors 52 and 54. The increase of the correlation coefficient from $C_\omega$ in successive imaging vectors indicates a decrease in the rotational speed of transducer 21.

Figure 7A:
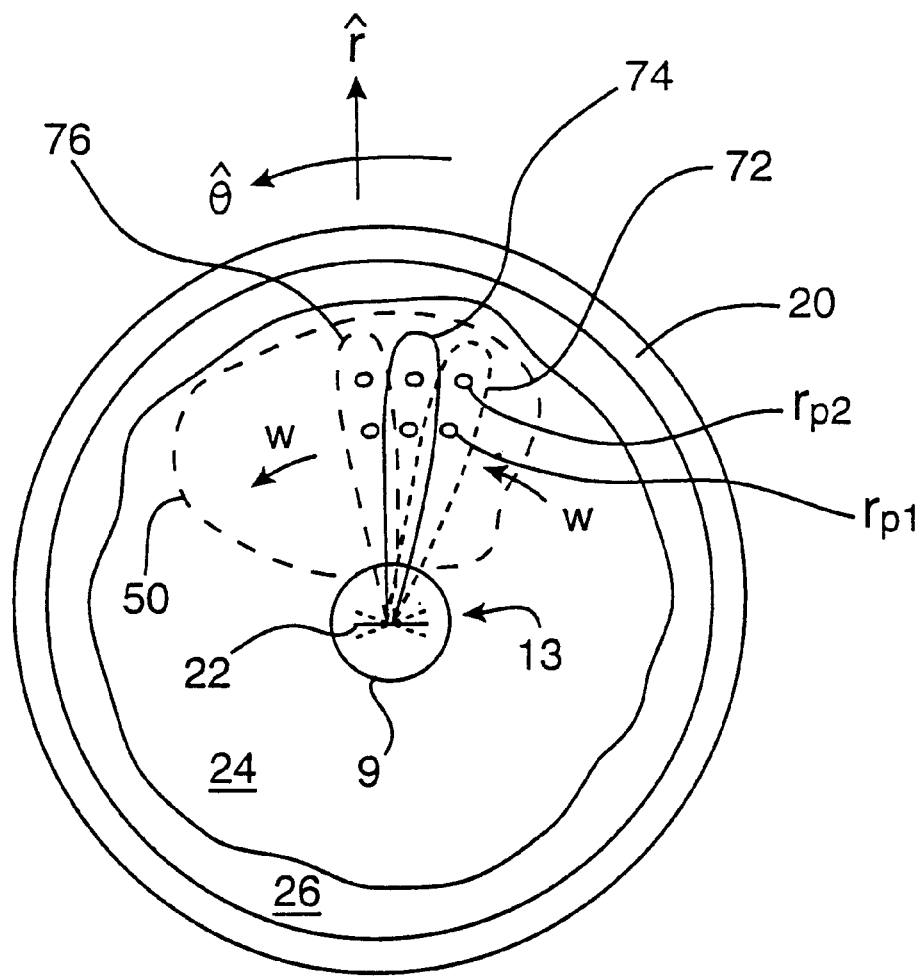
FIG. 7(a) is an exemplary diagram illustrating successive vectors for a transducer rotating uniformly, according to yet another specific embodiment of the present invention.
Figure 7B:
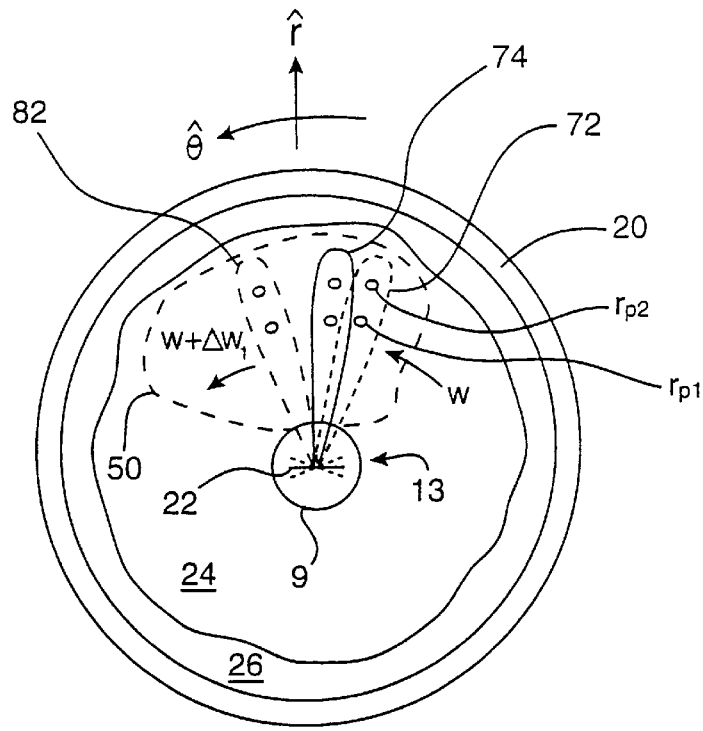
FIGS. 7(b)–7(c) are exemplary diagrams illustrating successive vectors for a non-uniformly rotating transducer which is increasing and decreasing, respectively, in rotational speed in comparison to the uniform rotational speed shown in FIG. 7(a).
Figure 7C:
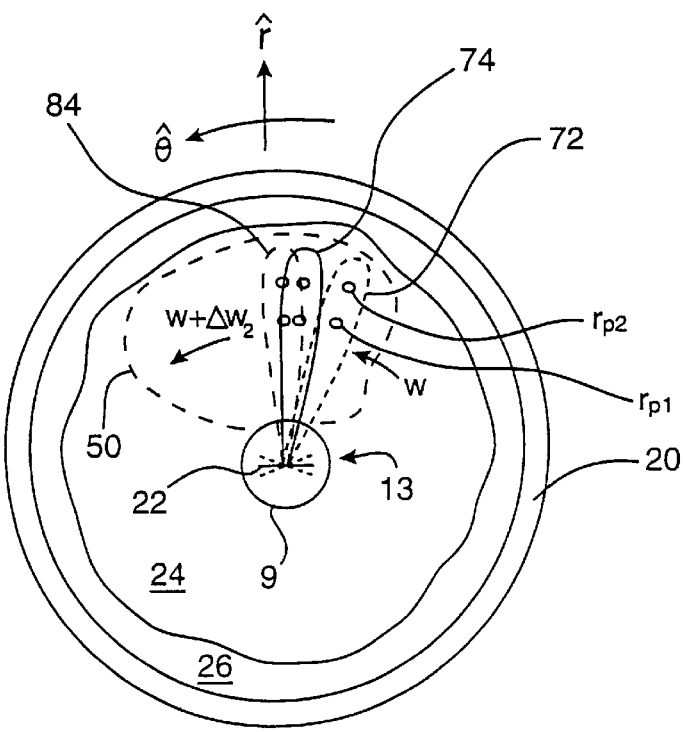

According to further specific embodiments which are similar to the embodiment discussed above for FIGS. 6(a)–6(c), correlation of blood speckle is used to track the rotation of the transducer. These embodiments also could utilize the general correlation expression given in equation 6 or 11 of the Barnea reference, in the 1-dimensional time/depth domain for multiple given ranges or depths ($r_{P1}$, $r_{P2}$, $r_{P3}$, etc.) in successive image vectors, in order to provide various measurements of the non-uniform rotation for greater accuracy of detection. The present embodiments, described in relation to FIGS. 7(a)–7(c), are herein discussed for two given depths ($r_{P1}$ and $r_{P2}$, where $r_{P1}$ is closer to the transducer than $r_{P2}$) merely for purposes of simplicity in explanation. In a similar manner as for the embodiment of FIGS. 6(a)–6(c), region 50 in the imaging scene where the image texture is full of speckle is selected for the embodiment of FIGS. 7(a)–7(c).

FIG. 7(a) is an exemplary diagram illustrating successive vectors for a transducer 22 rotating uniformly, according to the present specific embodiment. FIGS. 7(b)–7(c) are exemplary diagrams illustrating successive vectors for a non-uniformly rotating transducer which is increasing and decreasing, respectively, in rotational speed in comparison to the uniform rotational speed shown in FIG. 7(a). For simplicity, the transducer 22 is located substantially in the center of blood vessel 20, but it should be recognized that the discussion also applies when transducer 22 is off-center as long as region 50 of blood speckle exists for use with the present embodiment. As seen in FIG. 7(a), transducer 22 is rotating with a uniform rotational speed $\omega$ with successive image vectors (specifically, image vector 72 taken for $\theta_i$, image vector 74 taken for $\theta_{i+1}$, and image vector 56 taken for $\theta_{i+2}$) being uniformly separated by a uniform angular separation $\Delta\theta$. The correlations between each successive image vector (between 52 and 54, and between 54 and 56) at the same predetermined ranges $r_{P1}$ and $r_{P2}$ (we define the correlation at $r_{P1}$ between successive image vectors for uniformly rotating speed $\omega$ to be $C_{\omega 1}$, and the correlation at $r_{P2}$ between successive image vectors for uniformly rotating speed $\omega$ to be $C_{\omega 2}$) should be relatively high and substantially similar between successive image vectors which maintain about the same angular separation. The lack of fluctuation of the correlation coefficient in successive imaging vectors indicates a lack of fluctuation (i.e., uniform rotation) in the rotational speed of transducer 22.

Within region 50, the correlation coefficient at a particular range between successive image vectors should be low for values of the range that have a separation greater than the ultrasound beamwidth. In contrast, in blood speckle region 50, the correlation coefficient at a particular range between successive image vectors should be high for values of the range that have a separation less than the ultrasound beamwidth. Determining the correlation coefficients at more than one range value between successive image vectors enables greater accuracy of the detection of non-uniform rotation.

If the beamwidth measured in angle remains constant at each of the selected ranges $r_{P1}$ and $r_{P2}$ in the beam falling within region 50, then the correlation coefficients at both $r_{P1}$ and $r_{P2}$ between successive vectors should be substantially the same when the successive vectors maintain about the same angular separation (i.e., uniform rotation of transducer 21). For example, the correlation coefficients between successive vectors 72 and 74 at points $r_{P1}$ and $r_{P2}$ might be, respectively, $C_{\omega 1}=0.9$ and $C_{\omega 2}=0.9$, and these coefficients will remain substantially constant for successive vectors 74 and 76 when the transducer rotates uniformly. As seen in FIG. 7(b), transducer 22 rotates with a uniform rotational speed pX from image vector 72 taken for $\theta_i$ to image vector 74 taken for $\theta_{i+1}$, which are uniformly separated by a uniform angular separation $\Delta\theta$. However, transducer 22 starts to rotate with an increasing rotational speed $\omega+\Delta\omega_1$ from image vector 74 taken for $\theta_{i+1}$ to image vector 82 taken for $\theta_{i+2}$. However, the correlations between successive image vectors 74 and 82 at the predetermined ranges $r_{P1}$ and $r_{P2}$ (e.g., the correlations at $r_{P1}$ and at $r_{P2}$ between vectors 74 and 82 are each about 0.4) should both be lower than the correlations $C_{\omega 1}$ and $C_{\omega 2}$ between vectors 72 and 74, since successive image vectors 74 and 82 have a wider angular separation compared to the beamwidth. The decrease of the correlation coefficients from $C_{\omega 1}$ and $C_{\omega 2}$ in successive imaging vectors 74 and 82 indicates an increase in the rotational speed of transducer 22. In FIG. 7(c), transducer 22 rotates with a uniform rotational speed $\omega$ from image vector 72 taken for $\theta_i$ to image vector 74 taken for $\theta_{i+1}$, which are uniformly separated by a uniform angular separation Δθ. However, transducer 22 starts to rotate with a decreasing rotational speed ω–Δω$_2$ from image vector 74 taken for θ$_{i+1}$ to image vector 84 taken for θ$_{i+2}$. Again, the correlation between successive image vectors 72 and 74 at the same predetermined ranges r$_{P1}$ and r$_{P2}$ should be relatively high and are defined as C$_{ω1}$ and C$_{ω2}$, respectively. However, the correlations between successive image vectors 74 and 84 at the same predetermined ranges r$_{P1}$ and r$_{P2}$ (e.g., the correlations at r$_{P1}$ and at r$_{P2}$ between vectors 74 and 84 are each about 0.95) should be higher than the correlations C$_{ω1}$ and C$_{ω2}$ between vectors 72 and 74, since successive image vectors 74 and 84 have an even smaller angular separation compared to the beamwidth than image vectors 72 and 74. The increase of the correlation coefficients from C$_{ω1}$ and C$_{ω2}$ in successive imaging vectors 74 and 84 indicates a decrease in the rotational speed of transducer 21. Since the correlations at r$_{P1}$ and at r$_{P2}$ between vectors 74 and 82 should be the same (assuming the beamwidth measured in angle remains constant at each of the selected ranges r$_{P1}$ and r$_{P2}$), regardless of the increase or decrease from the correlations between vectors 72 and 74, the value of the correlation at r$_{P1}$ and the value of the correlation at r$_{P2}$ may be averaged if the values differ (the difference in values being attributed to noise).

If the beamwidth measured in angle increases from the selected range r$_{P1}$ to r$_{P2}$ in the beam falling within region 50, then the correlation coefficient between successive vectors at r$_{P1}$ will typically have the same percentage change as the correlation coefficient between successive vectors at r$_{P2}$, because the distance between points at r$_{P2}$ in successive vectors is less than the beamwidth at r$_{P2}$ by a greater amount than the distance between points at r$_{P1}$ in successive vectors is less than the beamwidth at r$_{P1}$. For example, the correlation coefficients between successive vectors 72 and 74 at points r$_{P1}$ and r$_{P2}$ might be, respectively, C$_{ω1}$=0.8 and C$_{ω2}$=0.9, and these coefficients will remain substantially constant for successive vectors 74 and 76 when the transducer rotates uniformly. As seen in FIG. 7(b), transducer 22 rotates with a uniform rotational speed ωfrom image vector 72 taken for θ$_i$ to image vector 74 taken for θ$_{i+1}$, which are uniformly separated by a uniform angular separation Δθ. However, transducer 22 starts to rotate with an increasing rotational speed ω+Δω$_1$, from image vector 74 taken for θ$_{i+1}$ to image vector 82 taken for θ$_{i+2}$. However, the correlations between successive image vectors 74 and 82 at the predetermined ranges r$_{P1}$ and r$_{P2}$ (e.g., the correlation at r$_{P1}$ between vectors 74 and 82 is about 0.72, and the correlation at r$_{P2}$ between vectors 74 and 82 is about 0.81) should both be lower by a similar percentage than the correlations C$_{ω1}$ and C$_{ω2}$ between vectors 72 and 74, since successive image vectors 74 and 82 at r$_{P2}$ have a narrower angular separation compared to the increased beamwidth at r$_{P2}$ and successive image vectors 74 and 82 at r$_{P1}$ have a wider angular separation compared to the decreased beamwidth at r$_{P1}$. The decrease of the correlation coefficients from C$_{ω1}$ and C$_{ω2}$ in successive imaging vectors 74 and 82 indicates an increase in the rotational speed of transducer 22. In FIG. 7(c), transducer 22 rotates with a uniform rotational speed ωfrom image vector 72 taken for θ$_i$ to image vector 74 taken for θ$_{i+1}$, which are uniformly separated by a uniform angular separation Δθ. However, transducer 22 starts to rotate with a decreasing rotational speed ω–Δω$_2$ from image vector 74 taken for θ$_{i+1}$ to image vector 84 taken for θ$_{i+2}$. Again, the correlation between successive image vectors 72 and 74 at the same predetermined ranges r$_{P1}$ and r$_{P2}$ should be relatively high and are defined as C$_{ω1}$ and C$_{ω2}$ respectively. However, the correlations between successive image vectors 74 and 84 at the same predetermined ranges r$_{P1}$ and r$_{P2}$ (e.g., the correlation at r$_{P1}$ between vectors 74 and 82 is about 0.88, and the correlation at r$_{P2}$ between vectors 74 and 82 is about 0.99) should be higher than the correlations $_{ω1}$ and C$_{ω2}$ between vectors 72 and 74, since successive image vectors 74 and 84 have an even smaller angular separation compared to the beamwidth than image vectors 72 and 74. The increase of the correlation coefficients from C$_{ω1}$ and C$_{ω2}$ in successive imaging vectors 74 and 84 indicates a decrease in the rotational speed of transducer 21.

In the embodiments discussed above for FIGS. 6(a)–6(c) and for FIGS. 7(a)–7(c), it should be recognized that the correlation between vectors would be governed by the given beamwidth of the transducer. Since the beamwidth (measured in angle) of the transducer may vary with r, r$_P$ is preferably selected such that it lies beyond the far-field of the transducer. The far-field of the transducer is determined by the expression $r_{far\text{-}field}=(A^2)/\lambda$ where A is the radius of the circular transducer and λ is the wavelength of the center frequency f$_0$ of the transducer.

Once non-uniform rotation is detected either by correlating echoes in a liquid-flushed catheter or by correlating blood speckle, conventionally known corrective actions can include re-distribution of the imaging vectors, either in transmission or display, in order to compensate for the non-uniform rotational speed and reduce or remove the distortion from the image.

While the invention has been particularly shown and described with reference to specific embodiments thereof, it will be understood by those skilled in the art that the foregoing and other changes in the form and details may be made therein without departing from the spirit or scope of the invention. It is therefore not intended that this invention be limited, except as indicated by the appended claims.

What is claimed is:

1. A method for detecting non-uniform rotation distortion in an ultrasound body lumen image, said method comprising the steps of:

providing a catheter probe within a body lumen, said catheter probe having a sheath and a transducer substantially centrally located within said sheath, wherein said transducer is mechanically controlled;

emitting an ultrasonic beam to produce echoes reflected from a bodily substance to obtain a given image vector;

sampling said echoes in a plurality of time windows for said given image vector;

correlating said sampled echoes in said plurality of time windows to determine existence of non-uniform rotational speed of said transducer.

2. The method of claim 1 further comprising the step of quantifying the non-uniform rotational speed of said transducer to compensate therefor.

3. The method of claim 2 wherein said bodily substance comprises blood speckle.

4. The method of claim 1 wherein a time t$_0$ between a beginning of successive windows in said plurality is greater than the time t$_s$=(2 r$_s$)/c between said ultrasonic beam being emitted by said transducer and a first echo received by said transducer.

5. The method of claim 4 wherein a slow down in the rotational speed of said transducer has occurred if a first correlation coefficient between a first window and a second window is less than a second correlation coefficient between said second window and a third window, and an increase in the rotational speed of said transducer has occurred if the first correlation coefficient between the first window and the second window is greater than the second correlation coefficient between said second window and the third window.

6. Apparatus for detecting non-uniform rotation distortion in an ultrasound body lumen image, said apparatus comprising:
a catheter for use within a body lumen, said catheter including:
a sheath, and
a transducer mechanically rotated within said catheter, wherein said transducer emits an ultrasonic beam and receives echoes of said ultrasonic beam from outside of said sheath; and
an image processor capable of being coupled to said transducer, said image processor including computer-readable program code fixed on tangible computer-readable medium for storing said computer-readable program, said computer-readable medium coupled to be read by said image processor, wherein said computer-readable program code performs a correlation on a plurality of segments in an image vector from said echoes of said ultrasonic beam to detect the non-uniformity of rotation of said transducer.

7. The apparatus of claim 6 wherein said received echos are reflected from a bodily substance.

8. The apparatus of claim 6 wherein a time $t_0$ between a beginning of successive windows in said plurality is greater than the time $t_s=(2\,r_s)/c$ between said ultrasonic beam being emitted by said transducer and a first echo received by said transducer.

9. The apparatus of claim 8 wherein a slow down in the rotational speed of said transducer has occurred if a first correlation coefficient between a first window and a second window is less than a second correlation coefficient between said second window and a third window, and an increase in the rotational speed of said transducer has occurred if the first correlation coefficient between the first window and the second window is greater than the second correlation coefficient between said second window and the third window.

10. A method for detecting non-uniform rotation distortion in an ultrasound body lumen image, said method comprising the steps of:
providing a catheter probe within a body lumen, said catheter probe having a transducer substantially centrally located therein, wherein said transducer is mechanically controlled;
emitting a plurality of ultrasonic beams to produce echoes reflected from a region outside said catheter probe to obtain a plurality of successive image vectors;
sampling said echoes at a predetermined range ($r_P$) for each of said successive image vectors, wherein $r_P$ for each of said successive image vectors is located within said region outside said catheter probe;
obtaining correlation coefficients for said sampled echoes at $r_P$ between each of said successive image vectors to determine changes in a rotational speed of said transducer.

11. The method of claim 10 wherein said obtaining step includes determining from a decrease in correlation coefficients that said rotational speed of said transducer has increased or determining from an increase in correlation coefficients that said rotational speed of said transducer has decreased.

12. The method of claim 10 wherein said predetermined range $r_P$ is selected to lie beyond the far-field of said transducer.

13. The method of claim 11 wherein said sampling step further includes sampling said echoes at a plurality of predetermined ranges for each of said successive image vectors, wherein said predetermined range $r_P$ is one of said plurality and a second predetermined range $r_{P2}$ is another one of said plurality, wherein $r_{P2}$ is selected to be within said region outside said catheter probe at a greater distance from said transducer than said $r_P$, and wherein said obtaining step further includes obtaining correlation coefficients for said sampled echoes at $r_{P2}$.

14. The method of claim 13 wherein said predetermined range $r_P$ and said second predetermined range $r_{P2}$ are each selected to lie beyond the far-field of said transducer.

15. The method of claim 14 wherein a beamwidth measured in angle of said ultrasonic beams remains constant at each of the predetermined ranges $r_P$ and $r_{P2}$.

16. The method of claim 15 wherein the correlation coefficients at both $r_{P1}$ and $r_{P2}$ between successive vectors should be substantially the same when said successive vectors maintain about the same angular separation.

17. The method of claim 15 wherein said successive vectors have increased their angular separation when the correlation coefficients at both $r_P$ and $r_{P2}$ between successive vectors respectively decrease, and wherein said successive vectors have decreased their angular separation when the correlation coefficients at both $r_P$ and $r_{P2}$ between successive vectors respectively increase.

18. The method of claim 14 wherein a beamwidth measured in angle of said ultrasonic beams increases from said predetermined range $r_P$ to said second predetermined range $r_{P2}$.

19. The method of claim 18 wherein said successive vectors have increased their angular separation when the correlation coefficients at both $r_P$ and $r_{P2}$ between successive vectors respectively decrease, and wherein said successive vectors have decreased their angular separation when the correlation coefficients at both $r_P$ and $r_{P2}$ between successive vectors respectively increase.

20. Apparatus for detecting non-uniform rotation distortion in an ultrasound body lumen image, said apparatus comprising:
a catheter for use within a body lumen, said catheter including:
a sheath, and
a transducer mechanically rotated within said catheter, wherein said transducer emits a plurality of ultrasonic beams to produce echoes reflected from a region outside of said sheath to obtain a plurality of successive image vectors; and
an image processor capable of being coupled to said transducer, said image processor including computer-readable program code fixed on tangible computer-readable medium for storing said computer-readable program, said computer-readable medium coupled to be read by said image processor, wherein said computer-readable program code samples said echoes at a predetermined range ($r_P$) for each of said successive image vectors, wherein $r_P$ for each of said successive image vectors is located within said region, and wherein said computer-readable program code also obtains correlation coefficients for said sampled echoes at $r_P$ between each of said successive image vectors to determine changes in a rotational speed of said transducer.

21. The apparatus of claim 20 wherein said computer-readable program code determines from a decrease in correlation coefficients that said rotational speed of said transducer has increased and/or determines from an increase in correlation coefficients that said rotational speed of said transducer has decreased.

* * * * *